United States Patent [19]

Leneau et al.

[11] Patent Number: 5,548,066

[45] Date of Patent: Aug. 20, 1996

[54] FAILURE OF PASSIVE TRANSFER IMMUNE SERUM AND METHOD OF MAKING SAME

[75] Inventors: Harry Leneau, Aurora, Ill.; William G. Skelly, Kansas City, Mo.

[73] Assignee: Central Biomedia, Inc., Irwin, Mo.

[21] Appl. No.: 349,010

[22] Filed: Dec. 2, 1994

[51] Int. Cl.$^6$ .............. C07K 16/00; C07K 1/34; A61K 39/395
[52] U.S. Cl. .............. 530/390.5; 530/389.1; 530/414; 530/829; 530/830; 530/861; 378/66; 424/130.1; 424/184.1
[58] Field of Search ............ 530/387.1, 390.5, 530/414, 829, 830, 861; 378/66; 424/130.1, 184.1

[56] References Cited

U.S. PATENT DOCUMENTS

| | | | |
|---|---|---|---|
| 2,386,725 | 10/1945 | Shean | 530/386 |
| 3,743,480 | 7/1973 | Falk | 422/21 |
| 4,349,539 | 9/1982 | Wampler | 424/227.1 |
| 4,665,159 | 5/1987 | Dobkin | 530/389.4 |
| 5,362,442 | 11/1994 | Kent | 422/22 |

OTHER PUBLICATIONS

Mangold et al. "Passive Transfer w/ Serum & IgG Antibodies of Irradiated Cercaria–Induced Resistance Against *Schistosoma Mansoni* In Mice".

J. Immunol. 136(7): 2644–2648 1986.

Primary Examiner—Mindy B. Fleisher
Assistant Examiner—Nancy J. Degen
Attorney, Agent, or Firm—Kokjer, Kircher, Bowman & Johnson

[57] ABSTRACT

An immunological serum and method of making same. The serum essentially consists of purified and concentrated materials, sometimes known as transfer factor, and immunoglobulins, expressed from the clotted blood of a donor group having known immunity. To produce the serum, a group of donors is chosen which includes known immunity, preferably to a wide variety of ailments. Blood is drawn from the donor group and allowed to clot. Thereafter, the blood is filtered to remove all cellular material, producing raw serum. This raw serum is then concentrated by removal of water. The concentrated serum is then sterilized, but not denatured, by freezing and gamma irradiation.

22 Claims, No Drawings

5,548,066

FAILURE OF PASSIVE TRANSFER IMMUNE SERUM AND METHOD OF MAKING SAME

BACKGROUND OF THE INVENTION

1. Field of the Invention

The present invention relates in general to serum for providing immunity in mammals, and methods of making same. In particular, the present invention relates to an improved serum for providing humoral and cellular immunity in mammals, especially infants, and methods of making same.

2. Description of the Related Art

As is well known, the immune system of mammals provides protection against disease and infection by various mechanisms. The immune system, however, may be suppressed for various reasons, or the immune system may have no inherited defense against a particular ailment. For example, the immune system of infant mammals is not fully developed for several days or weeks. To provide protection against disease and infection, a wide variety of serums are known. For example, in nature, mother's milk provides colostrum, which acts to impart immunity to infant mammals.

SUMMARY OF THE INVENTION

An object of the present invention is to provide an immunological serum.

Another object of the present invention is to provide such a serum which provides humoral and cellular immunity.

A further object of this invention is to provide such a serum which imparts short-term immunity to infant mammals.

A further object of the present invention is to provide a method of making such a serum, which includes drawing blood from a donor group having known immunity, permitting the blood to at least partially clot with rupturing of white blood cells, thereafter removing cellular material and concentrating the serum.

Yet another object of the present invention is to provide a method of sterilization for serums and other products, which includes freezing the product, subjecting the frozen product to gamma irradiation to a sufficient extent to sterilize but not denature, and thereafter thawing the product.

These and other objects are achieved by an immunological serum and method of making same. The serum includes purified and concentrated materials including immunoglobulins and other materials, sometimes known as transfer factor, expressed from the clotted blood of a donor group having known immunity. To produce the serum, a group of donors is chosen which includes known immunity, preferably to a wide variety of ailments. Blood is drawn from the donor group and allowed to clot with rupturing of white blood cells. Thereafter, the liquid portion of the blood is separated from the clotted material to produce the raw serum. The raw serum is then clarified to remove all cellular material, producing a clarified serum. This clarified serum is then concentrated by removal of components of 100,000 MW or smaller. The concentrated serum is then sterilized, but not denatured, by freezing and gamma irradiation.

DETAILED DESCRIPTION OF THE INVENTION

The immunological serum of the present invention is a purified and concentrated extract of blood. Although the exact mechanism(s) permitting the serum to impart immunity are not known, it is believed that the serum contains transfer factor released from the white blood cells in the extracted blood, and possibly other chemicals present in the extracted blood. This transfer factor is believed to provide information which is "read" by the immune system of the recipient to provide temporary immunity, typically on the order of six to eight weeks.

As the exact composition and operation of the serum is not known, the serum is best described by the method of its preparation.

To prepare the inventive serum, a plurality of blood donors are first identified. These donors are mature mammals, typically mammals of the same species for which the serum will be employed. For example, a herd of mature horses will make up the donor stock for the production of equine serum. By using mature mammals, it is assured that each donor will have been exposed to numerous different ailments during its lifetime, and will thus have immunity against at least a portion of such ailments. The use of a plurality of donors will therefore increase the number of ailments against which immunity has been developed. Where a specific ailment, such as rhodococcus in infant horses, is a widespread problem, it is preferred that at least a majority of the donors have been exposed to that ailment.

To achieve a consistent serum product, it is preferred that the donor group be relatively large. For example, a herd of two hundred or more horses would be a preferred donor group. Additionally, it is preferred that the donor group be chosen from differing geographic regions, such as by purchasing the horses from different states, although the donors would typically then be brought together into a single location. Additionally, it may be desirable to immunize the donor group, possibly on a periodic basis common to the particular vaccine, to maintain the immunity level of the donor group.

Once the donors have been identified, blood is drawn from the donors. Since the serum is refined directly from the blood, it is desired to obtain the maximum quantity of blood to thus obtain the maximum quantity of serum. This may be achieved by bleeding the donor to the point of death or by obtaining blood after the death of the mammals, such as from a slaughterhouse.

While such measures are available, it is preferred to identify and maintain a consistent donor group by repeated drawing of smaller quantities of blood. For example, drawing of blood once a week from horses, or once a month from humans. The frequency of the drawing will of course influence the quantity which may be safely drawn. In general, it is desired to draw the maximum amount of blood over the course of time without causing detriment to the health of the donor. This may dictate drawing small amounts with great frequency, or the maximum amount possible at a reduced frequency, depending upon the particular species.

For horses, it is preferred that each donor be bled on a weekly basis, with approximately twenty to thirty percent of the donor's blood being collected. The blood volume of the donor may be estimated by standard formulas available from the Center for Disease Control, such as 800 ml of blood per kg of body weight for horses. As such, for a horse weighing 700 kg, the blood volume is estimated to be (700 kg)(0.08 l/kg), or 56 liters of blood. Therefore, (56 l)(0.25), or 14 liters of blood may be drawn on a weekly basis.

The health of the donor is of course a consideration in this process if long-term bleeding is desired. Before bleeding is performed the mammal will be checked for general good health, and if the donor is in poor health the bleeding may be deferred until the next scheduled date. Beyond this, it is preferred that long-term health records be kept, preferably including more detailed information. In this regard, it is noted that production quantities of the present serum is a good indicator of the health of the donor.

Specifically, the serum is separated from the blood of the donor and consists of material from the immune system. In the preferred method for horses, detailed records are kept for the amount of serum produced from the blood as a yield percentage, such as 7 liters of serum from 14 liters of blood provides a yield of 50%.

In the preferred method for horses, records of the yield percentage are kept for each donor for each bleeding. These percentages may then be used to determine if the donor should be bled at the next scheduled time. In particular, if the action to be taken for horses is expressed as a function of yield percentages, a guideline may be expressed as follows: yield percentage ≦30%, rest; 31–35%, caution; 36–59%, normal; 60–64%, caution; ≧65%, rest. As may be seen, the donor is not bled if the serum yield is above or below the normal range. Such a yield percentage may indicate an underlying ailment. The subject may be bled, possibly in a reduced amount, in the caution ranges, depending upon the donor's history and/or further examination. In this regard, it has been found that a small percentage of horses consistently produce yield percentages around 60–62%.

The particular method for repetitive bleeding will of course differ from species to species, but is generally typical for methods of removing relatively large quantities of blood. For horses, the process is as follows.

Upon determining that the particular horse should be bled, the horse is haltered in a standard chute to restrict movement, especially of the head and neck. An area over the jugular vein is then clipped, cleaned and disinfected. This area is chosen above or below previous incisions which have not fully healed, and scar tissue. The area is then anesthetized, such as by 2 ml lidocaine injected subcutaneously above the vein using a 5 cc syringe with a 25 gauge×⅝" needle.

A tourniquet chain is then fastened loosely about the neck. After the anesthetic has taken effect (approximately 30–45 seconds for the noted lidocaine), an incision ½" long and no more than ½" deep is made over, and along the length of, the vein. The tourniquet chain is then tightened to cause the vein to protrude slightly. A bleeding needle, previously connected to flexible tubing and a sterile collection vessel, is then inserted into the vein, such that the blood drains into the vessel (preferably without splashing). The tubing is clamped upon filling the vessel, and the free end of the tube moved to a fresh, empty vessel to repeat the filling. This is continued until the desired amount of blood has been collected. The incision on the donor horse is then treated using standard methods.

While this method is generally standard, there are some important and unique aspects.

First, it is important that the donor horse remain calm prior to and during the procedure. Upon experiencing stress the horse may produce a large quantity of red blood cells. These cells take up volume in the collected blood, and reduce the serum yield.

Second, the blood may tend to coagulate on the interior of the collection vessel. Since the white blood cells will tend to be present on the exterior of clotted portions of the blood, some of the white blood cells may be trapped between the clot and the vessel wall. Since the harvesting of the white blood cell material is important to the serum, this is to be avoided or at least reduced. This may be achieved by coating the vessels with raw serum (defined more fully below) just prior to collection of the blood.

Once the blood has been collected, it is subjected to procedures for extracting the desired components. A first important step in this process is to permit each vessel of collected blood to sit at room temperature at least until substantial clotting has occurred. For horses, this is typically on the order of one hour. During this period the blood moves from body temperature to room temperature, and is exposed to air. This exposure to air permits the fibrinogen to change into fibrin, causing clotting of the blood.

This clotting period is an important aspect of the present invention. The clotting provides a rough separation of the cellular material from the liquid. Additionally, while the exact mechanism is not known, it is believed that the clotting period causes white blood cells to die and, for a percentage of such cells, to burst or rupture such that the chemical material therein is released from the cells. This material, possibly with other material in the blood, is referred to as "transfer factor". It is believed that this material remains within the serum and acts to provide "information" to the immune system of the recipient of the serum. This "information" may help to "program" white blood cells for particular viruses, similar to providing them with a memory of the virus, such that the white blood cells of the recipient respond quickly, and in a manner similar to a subject which has been vaccinated or is immune.

This period of non-refrigeration also causes a rough filtering of the collected blood. In particular, the clotted blood with the relatively heavy red blood cells will tend toward the bottom of the vessel, while the liquid plasma, immunoglobulins and transfer factor will be pushed toward the top. To assist in this process, and a process described below, it is preferred that the collection vessel be tall and thin, having proportions similar to a standard test tube. For example, in the method using horses, the vessel has a diameter of approximately 7 cm (2½") and a height of approximately 1.2 m (4'). This rather large height is chosen due to the large quantity of blood removed from horses, and other capacities, requiring the use of fewer or greater vessels, could be employed.

At this point it is believed that the liquid portion may be called raw serum and, subject to the filtering and sterilization processes described below, would be effective to impart immunity. However, to increase the yield, various other steps prior to filtration are preferred.

A first of these steps, after the collected blood has had sufficient time to clot, is refrigeration to approximately 2°–6° C. This refrigeration reduces the temperature of the blood from room temperature to the refrigeration temperature. Such cooling of course prevents growth of bacteria, mold, etc. Additionally, during this cooling the clotted blood settles further, and the clotted blood contracts. This contraction (and possibly the cooling) may cause a further percentage of the white blood cells to rupture. Additionally, the contraction of the clotted blood serves to express from the clot immunoglobulins and transfer factor which have been trapped therein. This refrigeration should last at least until the blood has achieved the refrigeration temperature, and preferably for about 14–18 hours, or overnight.

A second preferred step is physical pressing of the clotted blood. This pressing is believed to cause yet more rupturing of white cells, thus yielding even more of the transfer factor. Additionally, in a manner similar to the cooling contraction, the pressing serves to force immunoglobulins and transfer factor from the clot.

The preferred method of pressing is to insert a sterile weight into the refrigerated vessel of collected blood. For example, a cylinder having a close sliding fit within the vessel and a weight of approximately two pounds. As may be envisioned, the liquid material will flow about the cylinder until the cylinder has come to rest upon the clotted blood settled at the bottom of the vessel. It is preferred that the pressing weight be maintained in place for about 6–24 hours.

It is noted that the pressing can serve as a first active filtration step. The close fit of the weight serves to separate the liquid raw serum above and the solid material below, although a precision fit of the weight in the vessel is not required. Since this may serve as a first, rough, filtration step, it may conveniently be used to determine the quantity of raw serum produced for calculation of the yield percentage. Specifically, noting the height of the column of raw serum and knowing the diameter of the vessel provides the volume of raw serum produced.

At this point the filtering process proper begins. This further processing includes filtration to remove all cellular material. This filtration is achieved in multiple steps.

The first filtration step is a gross filtering. This may be achieved simply by pouring the contents of the vessel into a collection vat while holding a screen over the opening in the collection vessel. Where the high-yield steps of refrigeration and pressing have been used, the pressing cylinder still within the vessel may act in conjunction with the screen to filter, and the screen may mainly filter out the cylinder itself. Where these high-yield steps have not been taken, a finer filter screen may be desired. The clotted cells remaining within the vessel are properly disposed of, and the vessel sterilized for later use.

This is the preferred point for combining the serum from several different donors. As noted above, this will increase the range of effectiveness, as each donor will likely contribute slightly different material. It is noted, however, that the liquids from two or more donors could be combined at any point subsequent to the initial gross filtration step.

The raw serum thus removed will still contain a large amount of cells and cellular debris. As the next filtration step, the reclaimed liquid is then placed into a continuous flow centrifuge. For example, the liquid may be placed in a Sharples AS16NF continuous flow centrifuge, which will operate at approximately 13,000 to 15,000 rpm. The liquid is drawn off during this process while yet more of the cells and cellular debris is removed.

The liquid is then subjected to a further filtration step. This further step actually consists of several sub-steps, with the liquid being passed through several filters of progressively finer gauge. In particular, the liquid is passed through at least a 0.65 micron filter, then a 0.2 micron nominal filter, and then through a 0.2 micron absolute filter. As is known, the nominal gauge filters are less precise than absolute gauge, but also less expensive. By passing the liquid through the 0.2 nominal filter first, most of the bacteria, mold, and fibrin will be removed prior to passing through the 0.2 absolute filter. As such, the absolute gauge filter will require changing less often, reducing expense.

At this point the liquid has had essentially all solid cellular material removed. The transfer factor and immunoglobulins, however, remain in the liquid. The liquid may at this time be referred to as clarified serum. It is this clarified serum which may be used to coat the interior of the collection vessels.

This clarified serum could be used (after sterilization described below) as the final serum. However, it is preferred that the clarified serum be concentrated. This concentration reduces the volume and thus reduces the amount which must be shipped. Additionally, certain recipients, such as infant mammals, can not accept a large quantity of medication intravenously due to a lack of capacity. As such, concentration permits a full dosage of the serum to be administered.

The concentration is preferably performed by repeated ultra-filtration to remove water molecules, as is known in the art. Such filtration has a cut-off filter of between 10,000 and 100,000 mol. wt. During this process, samples of the clarified serum may be taken to determine if the serum has been sufficiently concentrated. It is preferred that the final serum be concentrated to about 2 to 6 times the clarified serum, and most preferably 2 to 4 times.

Determination of the concentration level is made by testing the amount of IgG within the serum. An initial test may be made of the clarified serum, and this result compared with the tests made upon the serum during the ultra-filtration process. For example, if the initial test results in the clarified serum having an IgG concentration of 1 g/100 ml, then the concentration process may be stopped when later tests report an IgG concentration of between about 2–6 g/100 ml, and preferably about 3 g/100 ml.

The determination of the IgG amount may be made by the radial immunodiffusion test. However, it is preferred that serum protein electrophoresis be performed on the whole serum to obtain an entire gamma globulin result. This is believed to be more accurate, and provides a clear indication of the IgG level.

Once the concentration process has been completed the concentrated unsterilized serum is bottled or packaged using standard procedures. For the horse serum, packaging in 300 ml vials is preferred.

Upon completion of the concentration and packaging process, the result is unsterilized serum. This of course implies that the next step is to sterilize the serum. While this sterilization is of course effected, it is important that the unsterilized serum not be denatured.

To provide sterilization without denaturing, the unsterilized serum is subjected to an inventive sterilization process. In this process the material to be sterilized, in this case packaged unsterilized serum, is frozen to a hard freeze condition. For the unsterilized serum, this is approximately $-29°$ C. ($-21°$ F.). While still frozen, the material is then subjected to sufficient gamma irradiation that the material is sterilized, but is not denatured. This level may vary for various species, but may be determined without undue experimentation. For the subject equine serum, 3.0–5.0 mrad is sufficient.

It is important that the material be sufficiently cold (hard frozen) such that the material remains frozen during the irradiation step, otherwise denaturing will occur. It is for this reason that the material is frozen to the relatively low temperature. If it is found that the irradiation process is sufficiently short, or refrigeration is provided during irradiation, then a higher temperature (though still below freezing) could be tolerated.

At this point the final serum has been achieved, although it is frozen. The packages of the serum are thus placed in refrigeration and allowed to thaw to the refrigeration temperature, where they are stored until use.

Use of the serum may be by standard intravenous infusion. For infant mammals, within approximately the first 12 hours of life, the serum may be ingested orally. However, after a few hours of life the mammal's gut will no longer permit passage of the large molecules present in the serum, and at that point intravenous use is required.

After administration, the serum has been found to provide cellular immunity similar to a vaccine, without the introduction of the virulent. In particular, it has been found that the serum may provide infant horses with excellent short term immunity to rhodococcus. This provides a clear indication that the serum is providing cellular immunity to the recipient.

In general, the present serum should provide protection against bacteria, fungi, mold, virus, etc. for which the donor group has immunity. While the present serum has been described with regard to rhodococcus in horses, the serum is should have such general utility for other equine ailments, and in particular ailments such as rhinopneumonitis, rotavirus, and pathogenic strains of *E. coli*. Additionally, the inventive serum should also be of utility for other mammals, such as farm and domestic mammals and humans. For cattle, one particular use would be to avoid Bovine Respiratory Disease Complex, a common ailment which occurs during transit to slaughter, and which can not be prevented with antibiotics due to imminent slaughter. Further bovine uses should include rotavirus and pathogenic strains of *E. coli*. For pigs, uses should include protection against pneumonia, TGE, rotavirus and pathogenic strains of *E. coli*. For goats, protection should be afforded against pneumonia, perfringens, rotavirus and pathogenic strains of *E. coli*. For dogs, the serum should be useful to prevent pneumonia, parvovirus, nonspecific dermatitis, and pathogenic strains of *E. coli*. In humans, a wide variety of vaccination uses are possible, including general vaccination for individuals with impaired immunity, such as is caused by the HIV virus. In particular, asthma, ARC and thrombocytopenia purpura should be suitable candidates for the present serum.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth is to be interpreted as illustrative, and not in a limiting sense.

What is claimed is:

1. A method of producing an immunological serum for a recipient animal to immunize said recipient animal against one or more diseases, comprising the steps of:

drawing blood from at least one donor animal of the same species as that of the recipient animal, said donor animal having known immunity for said one or more diseases;

permitting said blood to clot in such a manner that white blood cells within said blood rupture while the majority of the red blood cells within the blood remain intact, thereby producing clotted blood comprised of liquid and cellular material;

separating the liquid material from the cellular material in such a manner as to retrieve ruptured white blood cell components within the separated liquid material, said separated liquid material comprising raw serum;

clarifying said raw serum to produce a clarified serum;

concentrating said clarified serum to produce a concentrated serum; and sterilizing, without denaturing, said concentrated serum by subjecting the concentrated serum to gamma irradiation to produce the immunological serum.

2. A serum product produced by the method of claim 1.

3. The method of claim 1, wherein said drawing step comprises drawing blood from a donor group consisting of more than one hundred of said at least one donor animal.

4. The method of claim 1, further comprising the step, subsequent to said clotting and prior to said removing, of refrigerating said blood.

5. A serum product produced by the method of claim 4.

6. The method of claim 4, further comprising the step, subsequent to said refrigerating and prior to said removing, of physically pressing upon said clotted blood.

7. A serum product produced by the method of claim 6.

8. The method of claim 1, wherein said step of removing said liquid material includes filtering with a 0.2 micron filter.

9. The method of claim 1, comprising the further step, subsequent to said removing, and prior to said sterilizing, of concentrating said coating serum.

10. A serum product produced by the method of claim 9.

11. The method of claim 9, wherein said concentration step consists of repeated ultrafiltration of said clarified serum until a level of IgG per volume within said clarified serum has reached a level 2 to 5 times that prior to concentration.

12. A serum product produced by the method of claim 11.

13. The method of claim 1, wherein said sterilization step includes:

freezing said serum; and
    while maintaining the serum in a frozen state, subjecting said serum to gamma irradiation for a period sufficient to sterilize, but insufficient to denature.

14. A serum product produced by the method of claim 13.

15. The method of claim 13, wherein said step of gamma irradiation includes irradiating to about 3.0–5.0 mrad.

16. A serum product produced by the method of claim 15.

17. The method of claim 1, wherein said blood is drawn from at least one donor animal selected from the group consisting of at least one living animal, at least one deceased animal, and a combination thereof.

18. A serum product produced by the method of claim 17.

19. The method of claim 1, wherein said clarifying step is selected from the group consisting of centrifuging said raw serum, filtering said raw serum, and a combination thereof.

20. A serum product produced by the method of claim 19.

21. The method of claim 1 wherein said concentration step comprises removing components of a size 100,000 MW or smaller from said clarified serum.

22. A serum product produced by the method of claim 21.

* * * * *